(12) United States Patent
Al-Amin et al.

(10) Patent No.: US 12,190,257 B2
(45) Date of Patent: *Jan. 7, 2025

(54) SYSTEMS AND METHODS FOR GATING A STEP COUNT

(71) Applicant: Verily Life Sciences LLC, South San Francisco, CA (US)

(72) Inventors: Fuad Al-Amin, Milpitas, CA (US); Ali Shoeb, San Rafael, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/516,258

(22) Filed: Nov. 21, 2023

(65) Prior Publication Data
US 2024/0160968 A1 May 16, 2024

Related U.S. Application Data

(63) Continuation of application No. 16/436,082, filed on Jun. 10, 2019, now Pat. No. 11,861,517, which is a
(Continued)

(51) Int. Cl.
G06N 7/01 (2023.01)
A63B 24/00 (2006.01)

(52) U.S. Cl.
CPC ........... G06N 7/01 (2023.01); A63B 24/0062 (2013.01); *A63B 2220/17* (2013.01); *A63B 2220/40* (2013.01); *A63B 2230/202* (2013.01)

(58) Field of Classification Search
CPC .......................... G06N 7/005; A63B 24/0062; A63B 2220/17; A63B 2220/40; A63B 2230/202
See application file for complete search history.

(56) References Cited

U.S. PATENT DOCUMENTS 10,360,510 B1 7/2019 Al-Amin et al.
11,504,029 B1 * 11/2022 Martin .................. H04W 4/027
(Continued)

OTHER PUBLICATIONS

U.S. Appl. No. 15/496,095 , "Final office Action", mailed Nov. 3, 2017, 11 pages.
(Continued)

*Primary Examiner* — Malina D. Blaise
(74) *Attorney, Agent, or Firm* — Kilpatrick Townsend & Stockton LLP

(57) ABSTRACT

The present disclosure relates to activity monitoring systems and methods for gating whether or not steps should be counted in an observation window based on whether a decision tree concludes there are consecutive step activities (versus no activity or other activities) in the observation window. Particularly, certain aspects are directed to a method that includes obtaining acceleration data for an observation window of an accelerometer, inputting two or more characteristics of the acceleration data into a decision tree to determine activity occurring within the observation window, assigning a first class to the observation window when the determined activity is associated with consecutive steps, assigning a second class to the observation window when the determined activity is not associated with consecutive steps, and when the first class is assigned to the observation window, determining a step count for the observation window using frequency analysis.

20 Claims, 12 Drawing Sheets

Related U.S. Application Data continuation of application No. 15/496,095, filed on Apr. 25, 2017, now Pat. No. 10,360,510.

(56) References Cited

U.S. PATENT DOCUMENTS

| | | | | |
|---|---|---|---|---|
| 11,704,431 | B2* | 7/2023 | Kraus | H04L 63/0414 726/26 |
| 2013/0085700 | A1* | 4/2013 | Modi | G01C 22/006 702/160 |
| 2014/0074431 | A1* | 3/2014 | Modi | G01C 22/006 702/160 |
| 2016/0066844 | A1* | 3/2016 | Venkatraman | A61B 5/318 600/509 |
| 2016/0354014 | A1* | 12/2016 | Lobner | A61B 5/1118 |
| 2017/0067933 | A1* | 3/2017 | Miller | G01C 22/006 |
| 2022/0093230 | A1* | 3/2022 | Gupta | A63B 24/0062 |

OTHER PUBLICATIONS

U.S. Appl. No. 15/496,095, Non-Final Office Action, Mailed on Jul. 12, 2017, 18 pages.

U.S. Appl. No. 15/496,095, Non-Final Office Action, Mailed on Feb. 28, 2019, 7 pages.

U.S. Appl. No. 15/496,095, Notice of Allowance, Mailed on Apr. 18, 2019, 8 pages.

U.S. Appl. No. 16/436,082, Final Office Action, Mailed on Dec. 2, 2022, 13 pages.

U.S. Appl. No. 16/436,082, Non-Final Office Action, Mailed on May 5, 2022, 12 pages.

U.S. Appl. No. 16/436,082, Notice of Allowance, Mailed on Aug. 23, 2023, 8 pages.

Harris, "New Blood Sugar Monitor for Diabetes—With a Chicago Connection", Available online at: https://www.chicagotribune.com/business/ct-confidential-tullman-diabetes-0910-biz-20140910-column.html, Sep. 10, 2014, 3 pages.

Loreto et al., "Make Your Diabetic Patients Walk—Long-term Impact of Different Amounts of Physical Activity on Type 2 Diabetes", Diabetes Care, vol. 28, No. 6, Jun. 2005, pp. 1295-1302.

Neithercott, "Monitor Your Glucose With the Apple Watch", Diabetes Forecast—the Healthy Living Magazine, Available online at: https://www.diabetes.org/healthy-living, Apr. 2015, 3 pages.

Park et al., "Online Pose Classification and Walking Speed Estimation Using Handheld Devices", Proceedings of the 2012 ACM Conference on Ubiquitous Computing., Sep. 2012, 10 pages.

* cited by examiner

| Activity | | Length |
|---|---|---|
| stationary | | 30 s |
| 1.5 mph walk | | 120 s |
| stationary | | 30 s |
| 2.0 mph walk | | 120 s |
| stationary | | 30 s |
| 3.0 mph walk | | 120 s |
| stationary | | 30 s |
| Noise | Sitting | 60 s |
| | Twisting (side to side) | 60 s |
| | Leaning (front to back) | 60 s |
| | Standing | 60 s |
| stationary | | 30 s |
| Outdoor Free Walk | | 600 s |
| stationary | | 30 s |
| stationary | | 30 s |
| 5.0 mph run | | 120 s |
| stationary | | 30 s |
| 7.0 mph run | | 120 s |
| stationary | | 30 s | ns and Methods for Gating a
SYSTEMS AND METHODS FOR GATING A STEP COUNT

CROSS-REFERENCE TO RELATED APPLICATIONS

This application is a continuation of U.S. application Ser. No. 16/436,082, filed Jun. 10, 2019, which is a continuation of U.S. application Ser. No. 15/496,095, filed Apr. 25, 2017, the disclosures of which are incorporated by reference herein in their entities.

FIELD OF THE INVENTION

The present disclosure relates to activity monitoring systems and methods, and in particular to systems and methods for gating whether or not steps should be counted in an observation window based on whether a decision tree concludes there are consecutive step activities (versus no activity or other activities) in the observation window.

BACKGROUND

Diabetes is a disease in which the body's ability to produce or respond to the hormone insulin is impaired, resulting in abnormal metabolism of carbohydrates and elevated levels of glucose in the blood and urine. Prevention and treatment of diabetes include maintaining a healthy diet, regular physical exercise, a normal body weight, and avoiding use of tobacco products. In particular, it has been found that daily walking can have a positive effect on the health of diabetic and pre-diabetic patients in terms of reducing insulin resistance, lipid levels, and the visceral fat area. For example, walking more than 6500 steps daily at 2-3 km/h has been found to be clinically beneficial to overweight and obese individuals at risk of type 2 diabetes. A major challenge in developing an activity monitor for diabetic and pre-diabetic patients that monitors steps taken within the 2-3 km/h band is that while 6500 steps at 2-3 km/h takes roughly 90 minutes of continuous walking, the normal recorded activity of taking steps may be cumulative over the entire day and may be taken in isolated activities throughout the day, including steps derived from normal day-to-day activities (walking to meetings, cars, etc.). Due to this sporadic nature of activity performance, it can be difficult to judge a level of activity for a diabetic or pre-diabetic patient on any given day.

An activity monitor such as a pedometer can be used to improve the assessment of a level of activity for a diabetic or pre-diabetic patient based on a determined number of user's steps taken, distance traveled, and/or calories expended through-out a given day. Conventional pedometers use a built-in motion sensor (e.g., accelerometer) for detecting the orientation and/or movement of the pedometer, which may represent movement of the user attached to the pedometer. For example, when the pedometer is attached to a user, signals received from the motion sensor can be analyzed to determine (i) movement of the user, (ii) whether the movement is the user taking a step, (iii) a count for the number of steps determined to have been taken, (iv) a distance travelled by the steps, and/or (v) calories expended by taking the steps. Algorithms for analyzing the signals to determine movement of the user and whether the movement is the user taking a step (e.g., walking or running) can vary based on a number of factors including where on the user's body the pedometer is attached, processing power of the pedometer, memory or storage available for the pedometer, energy or power requirements of the pedometer, size constraints of the pedometer, material used to construct the pedometer, etc.

BRIEF SUMMARY

Various embodiments relate to a system including one or more processors and a memory coupled to the one or more processors. The memory is encoded with a set of instructions configured to perform a process including obtaining acceleration data for an observation window of an accelerometer; inputting two or more characteristics of the acceleration data into a decision tree to determine activity occurring within the observation window; determining that the activity within the observation window is associated with consecutive steps; assigning a first class to the observation window based on the determination that the activity is associated with the consecutive steps; and determining a step count for the observation window using frequency analysis based on the assignment of the first class to the observation window.

In accordance with some aspects, the two or more characteristics include an L1 Difference Norm, an L2 Difference Norm, a Fast Fourier Transform (FFT) Peak Frequency, an FFT Spectral Entropy, and FFT Total Energy. In accordance with other aspects, each of the two or more characteristics is selected without replication from the group consisting of: an L1 Difference Norm, an L2 Difference Norm, an FFT Peak Frequency, an FFT Spectral Entropy, and FFT Total Energy.

Optionally, determining the activity occurring within the observation window includes: determining a probability for each of one or more activities occurring within the observation window; and determining the activity with the greatest probability of occurring within the observation window based on the determined probabilities for of the one or more activities.

In accordance with some aspects, the first class is a low activity class or a high activity class, the frequency analysis includes integrating a dominant frequency in the observation window over a width of the observation window, and/or the width of the observation window is 5.12 seconds.

In accordance with certain aspects, the process further includes obtaining additional acceleration data for another observation window of the accelerometer; inputting the two or more characteristics of the additional acceleration data into the decision tree to determine activity occurring within the another observation window; determining that the activity within the another observation window is not associated with consecutive steps; assigning a second class to the another observation window based on the determination that the activity is associated with the consecutive steps; and incrementing a count of the second class in a database and stopping processing of the additional acceleration data for the another observation window without determining a step count for the another observation window.

In accordance with some aspects, the second class is a no activity class or other activity class, incrementing a count of the first class in a database and adding the determined step count for the observation window to a total step count stored in the database, and/or the system further includes a continuous glucose monitoring device and the accelerometer.

Optionally, the accelerometer includes a 12.5 Hz sampling rate, the observation window has a width of 5.12 seconds, and there are 64 samples within the observation window, and the process further includes, prior to inputting the two or more characteristics, normalizing magnitudes of the 64 samples to be zero mean, and calculating a vector X, and the vector X is used to calculate the two or more characteristics of the acceleration data.

In accordance with some aspects, the process further includes reporting a glucose reading with a contextual label based on the count of the first class and the step count, and/or the process further includes correcting a glucose reading based on the count of the first class and the step count.

Other embodiments relate to a non-transitory computer readable storage medium storing instructions that, when executed by one or more processors of a computing system, cause the computing system to perform operations including obtaining acceleration data for an observation window of an accelerometer; inputting two or more characteristics of the acceleration data into a decision tree to determine activity occurring within the observation window; determining that the activity within the observation window is associated with consecutive steps; assigning a first class to the observation window based on the determination that the activity is associated with the consecutive steps; and determining a step count for the observation window using frequency analysis based on the assignment of the first class to the observation window.

In accordance with some aspects, each of the two or more characteristics is selected without replication from the group consisting of: an L1 Difference Norm, an L2 Difference Norm, a Fast Fourier Transform (FFT) Peak Frequency, an FFT Spectral Entropy, and FFT Total Energy.

In accordance with certain aspects, the operations further include obtaining additional acceleration data for another observation window of the accelerometer; inputting the two or more characteristics of the additional acceleration data into the decision tree to determine activity occurring within the another observation window; determining that the activity within the another observation window is not associated with consecutive steps; assigning a second class to the another observation window based on the determination that the activity is associated with the consecutive steps; and incrementing a count of the second class in a database and stopping processing of the additional acceleration data for the another observation window without determining a step count for the another observation window.

Optionally, the first class is a low activity class or a high activity class, and the second class is a no activity class or other activity class.

In accordance with certain aspects, the operations further include normalizing magnitudes of the acceleration data to be zero mean, and calculating a vector X for the acceleration data, wherein the vector X is used to calculate the two or more characteristics of the acceleration data, and calculating a Fast Fourier Transform (FFT) for the vector X of the first set of acceleration data and the second set of acceleration data, respectively.

Optionally, the determining the step count comprises detecting and adjusting for harmonics by scaling a magnitude of the FFT for the acceleration data, and the detecting and adjusting for the harmonics comprises selecting a binary spectrum weight function for the FFT of the acceleration data.

Other embodiments relate to a method for monitoring activity. The method includes obtaining, at a computer system, a first set of acceleration data for a first observation window of an accelerometer; and determining, at the computer system, characteristics of the first set of acceleration data. The characteristics include an L1 Difference Norm, an L2 Difference Norm, a Fast Fourier Transform (FFT) Peak Frequency, an FFT Spectral Entropy, and FFT Total Energy. The method further includes determining, at the computer system, a probability for each of one or more activities occurring within the first observation window based on the determined characteristics; determining, at the computer system, a first activity with a greatest probability of occurring within the first observation window is associated with walking based on the determined probabilities for of the one or more activities occurring within the first observation window; assigning, at the computer system, a first class to the first observation window based on the determination that the activity is associated with the walking; obtaining, at the computer system, a second set of acceleration data for a second observation window of the accelerometer; determining, at the computer system, the characteristics of the second set of acceleration data; determining, at the computer system, a probability for each of one or more activities occurring within the second observation window based on the determined characteristics; determining, at the computer system, a second activity with a greatest probability of occurring within the second observation window is associated with running based on the determined probabilities for of the one or more activities occurring within the second observation window; assigning, at the computer system, a second class to the second observation window based on the determination that the activity is associated with the running; and determining, at the computer system, a first step count for the first observation.

In accordance with some aspects, the method further includes normalizing, at the computer system, magnitudes of the first set of acceleration data and the second set of acceleration data to be zero mean; and calculating a vector X for the first set of acceleration data and the second set of acceleration data, respectively. The vector X is used to calculate the characteristics of the first set of acceleration data and the second set of acceleration data, respectively. The method may further include calculating, at the computer system, a Fast Fourier Transform (FFT) for the vector X of the first set of acceleration data and the second set of acceleration data, respectively.

Optionally, the determining the first step count and the second step count includes detecting and adjusting for harmonics by scaling a magnitude of the FFT for the first set of acceleration data and the second set of acceleration data, respectively; the detecting and adjusting for the harmonics includes selecting a first binary spectrum weight function for the FFT of the first set of acceleration data and a second binary spectrum weight function for the FFT of the second set of acceleration data; and/or the first binary spectrum weight function is different from the second binary spectrum weight function.

BRIEF DESCRIPTION OF THE DRAWINGS

The present invention will be better understood in view of the following non-limiting figures, in which.

DETAILED DESCRIPTION

I. Introduction

Figure 1:
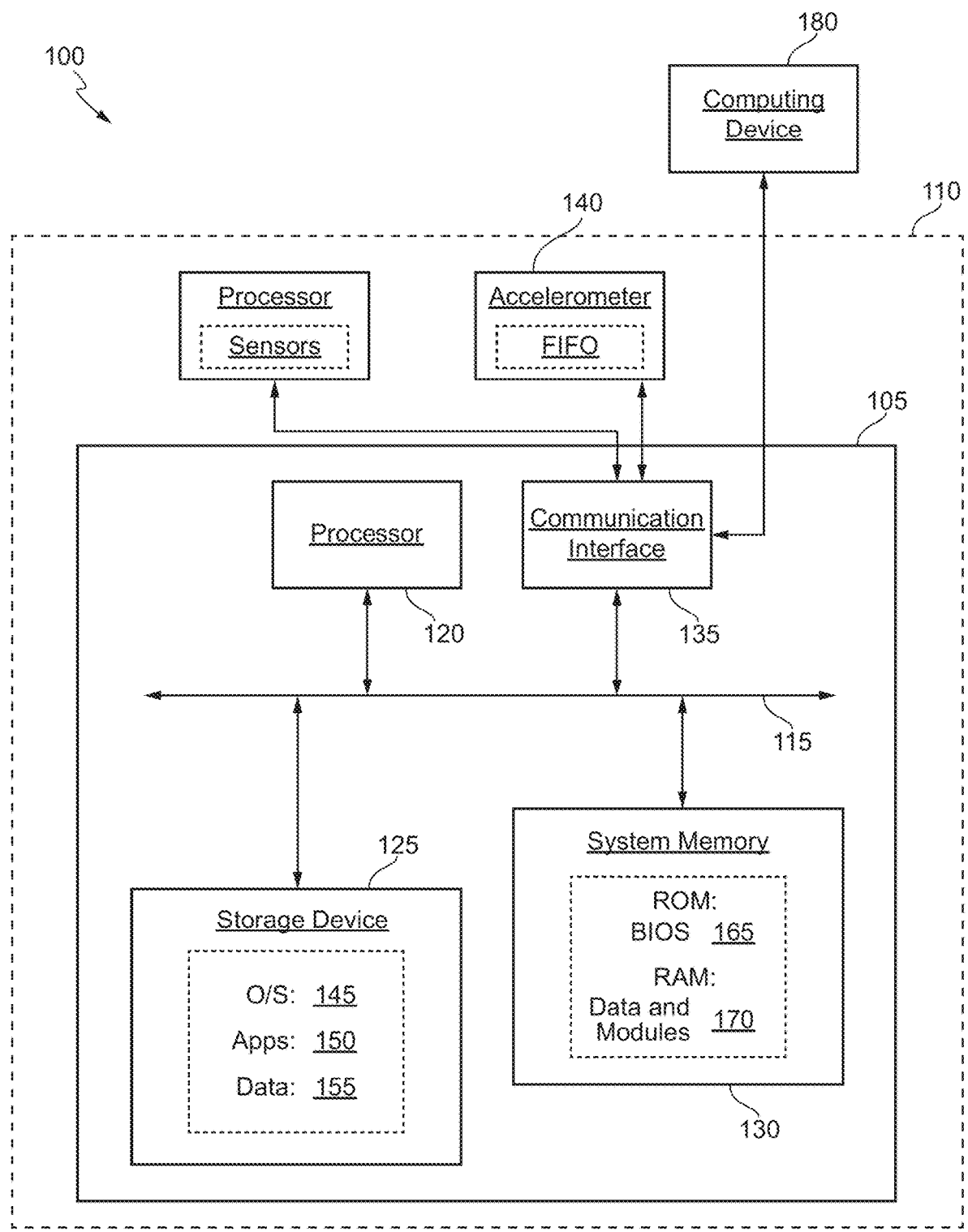
FIG. 1 shows an illustrative architecture of a computing system implemented in accordance with some embodiments.

Various embodiments are directed to an activity monitoring system in a continuous glucose monitor. The activity monitoring system is configured to detect movement of a user, determine whether the movement of the user includes the user taking consecutive steps, and determine how many consecutive steps the user has taken over a period time. A problem associated with conventional activity monitoring systems and methods is that they utilize complex algorithms that require extensive processing power, a large amount of memory or storage, and a rechargeable power or energy source for counting steps. Moreover, conventional activity monitoring systems typically demonstrate high error rate (e.g., up to 60% error rate) for determining steps taken during certain physical activities such as walking on a treadmill. This error rate trickles down and undesirably impacts the overall step count of the conventional activity monitoring systems and methods.

To address these problems, various embodiments described herein are directed to activity monitoring systems and methods capable of achieving minimal error rate in an environment, such as a continuous glucose monitoring system (e.g., including one-time use or disposable continuous glucose monitors), with limited processing and power resources. In particular, processes were developed that include gating whether or not steps should be counted in an observation window based on whether a decision tree concludes there are consecutive step activities (versus no activity or other activities) in the observation window. For example, various embodiments of the present disclosure include a system including one or more processors and a memory coupled to the one or more processors. The memory is encoded with a set of instructions configured to perform a process including obtaining acceleration data for an observation window of an accelerometer, inputting two or more characteristics of the acceleration data into a decision tree to determine activity occurring within the observation window, assigning a first class (e.g., a low activity class) to the observation window when the determined activity is associated with consecutive steps, assigning a second class (e.g., a no activity class) to the observation window when the determined activity is not associated with consecutive steps, and when the first class is assigned to the observation window, determining a step count for the observation window using frequency analysis.

Advantageously, these approaches provide activity monitoring systems and methods that are capable of achieving minimal error rate in an environment such as a continuous glucose monitoring system with limited processing and power resources. For example, the decision tree can be implemented with a low power budget (e.g., a simple tree of conditionals), and provides powerful non-linear classification capabilities of a multi-dimensional search space. The non-linear classification may be used to gate whether or not steps should be counted in an observation window, and consequently saves on computation power and increases robustness of the overall step counting process.

II. Activity Monitoring System

FIG. 1 is an illustrative architecture of a computing system 100 implemented in various embodiments. The computing system 100 is only one example of a suitable computing system and is not intended to suggest any limitation as to the scope of use or functionality of the various embodiments. Also, computing system 100 should not be interpreted as having any dependency or requirement relating to any one or combination of components illustrated in computing system 100.

As shown in FIG. 1, computing system 100 includes a computing device 105. The computing device 105 can be resident on a network infrastructure such as within a cloud environment, or may be a separate independent computing device (e.g., a computing device implemented within the environment of a medical device 110 such as a continuous glucose monitor). The computing device 105 may include a bus 115, processor 120, a storage device 125, a system memory (hardware device) 130, and a communication interface 135.

The bus 115 permits communication among the components of computing device 105. For example, bus 115 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 105.

The processor 120 may be one or more integrated circuits, printed circuits, controllers, microprocessors, or specialized dedicated processors that include processing circuitry operative to interpret and execute computer readable program instructions, such as program instructions for controlling the operation and performance of one or more of the various other components of computing device 105 for implementing the functionality, steps, and/or performance of the embodiments discussed herein. In certain embodiments, processor 120 interprets and executes the processes, steps, functions, and/or operations, which may be operatively implemented by the computer readable program instructions. For example, processor 120 can retrieve, e.g., import and/or otherwise obtain acceleration data from an accelerometer 140, input two or more characteristics of the acceleration data into a decision tree to determine activity occurring within an observation window, assign a first class to the observation window when the determined activity is associated with consecutive steps, assign a second class to the observation window when the determined activity is not associated with consecutive steps, and when the first class is assigned to the observation window, determine a step count for the observation window using frequency analysis. In embodiments, the information obtained or generated by the processor 120, e.g., accelerometer data, timestamps, a tally for various classifications, step counts for observations windows, a total step count, error codes, etc., can be stored in the storage device 125.

The storage device 125 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of computing device 105. In various embodiments, storage device 125 may store operating system 145, application programs 150, and/or program data 155. In some embodiments, the application programs 150, and/or program data 155 may include a database, index, or table, and algorithms such as an activity classification algorithm that includes components for pre-processing acceleration data, components for calculating characteristics of the acceleration data, a decision tree component to classify an observation window, and a step counting algorithm to quantify the number of steps taken by a user during a predetermined period of time, which provide the instructions for execution of processor 120.

The system memory 130 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 165 (BIOS) including the basic routines that help to transfer information between the various other components of computing device 105, such as during start-up, may be stored in the ROM. Additionally, data and/or program modules 170, such as at least a portion of operating system 145, application programs 150, and/or program data 155, that are accessible to and/or presently being operated on by processor 120, may be contained in the system memory 130.

The data and/or program modules 170 may include a motion data collector class that is configured to log activity histograms, step counts, and error status to the database at intervals (e.g., timer driven), and an activity monitor class that contains a comprehensive high level feature manager, and initialization, start, stop, error recovery, and interrupt service routines. The activity monitor class is configured to drive the accelerometer, and push data through the algorithms. The data and/or program modules may further include an accelerometer class configured to expose all necessary accelerometer behavior required to implement the step count features, and an activity classifier class that contains activity classification and step counter algorithm implementations and configured to maintain activity histograms and step counts. The data and/or program modules 170 may further include a controller class that contains a multi-slave serial peripheral interface device driver, a decision tree class configured to complete decision tree implementation with evaluation, and a math operation class configured to calculate characteristics of acceleration data including (i) the L1 Difference Norm, (ii) the L2 Difference Norm, (iii) the FFT Peak Frequency, (iv) the FFT Spectral Entropy, and (iv) the FFT Total Energy.

The communication interface 135 may include any transceiver-like mechanism (e.g., a network interface, a network adapter, a modem, or combinations thereof) that enables computing device 105 to communicate with remote devices or systems, such as medical device 110, accelerometer 140, a mobile device or other computing devices 180 such as, for example, a server in a networked environment, e.g., cloud environment. For example, computing device 105 may be connected to remote devices or systems via one or more local area networks (LAN) and/or one or more wide area networks (WAN) using communication interface 135.

As discussed herein, computing system 100 may be configured to gate whether or not steps should be counted in an observation window based on whether a decision tree concludes there are consecutive step activities (versus no activity or other activities) in the observation window. In particular, computing device 105 may perform tasks (e.g., process, steps, methods and/or functionality) in response to processor 120 executing program instructions contained in non-transitory machine readable storage medium, such as system memory 130. The program instructions may be read into system memory 130 from another computer readable medium (e.g., non-transitory machine readable storage medium), such as data storage device 125, or from another device via the communication interface 135 or server within or outside of a cloud environment. In some embodiments, hardwired circuitry of computing system 100 may be used in place of or in combination with the program instructions to implement the tasks, e.g., steps, methods and/or functionality, consistent with the different aspects discussed herein. Thus, the steps, methods and/or functionality disclosed herein can be implemented in any combination of hardware circuitry and software.

III. Activity Monitoring Processes

Figure 2:
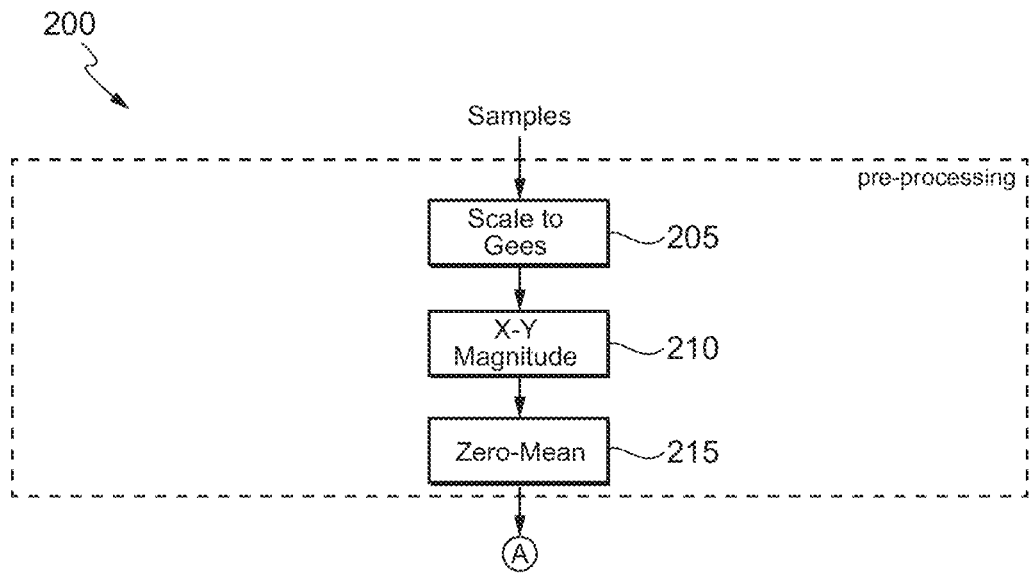
FIG. 2 shows an exemplary flow for preparing or preprocessing acceleration data obtained from an accelerometer in accordance with some embodiments.
Figure 3:
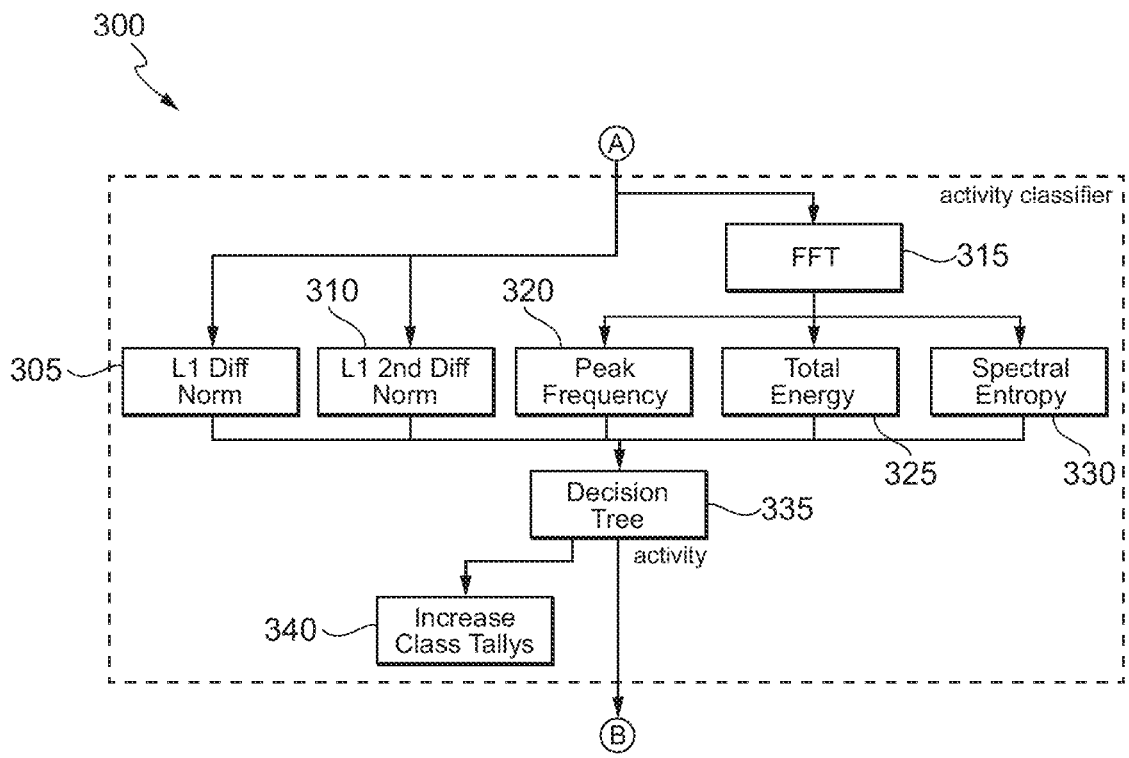
FIG. 3 shows an exemplary flow for assigning an activity class to an observation window in accordance with some embodiments.
Figures 5, 6:
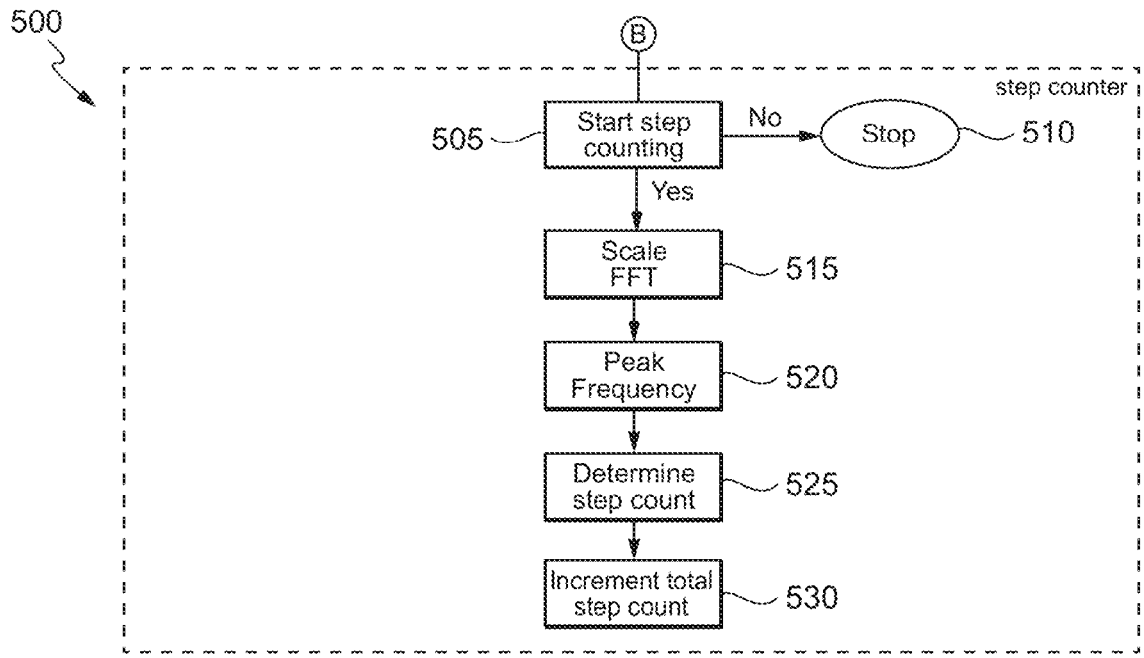
FIG. 5 shows an exemplary flow for counting steps in accordance with some embodiments.
FIG. 6 shows a list of activities performed using the activity monitoring system in accordance with some embodiments.
Figure 7A:
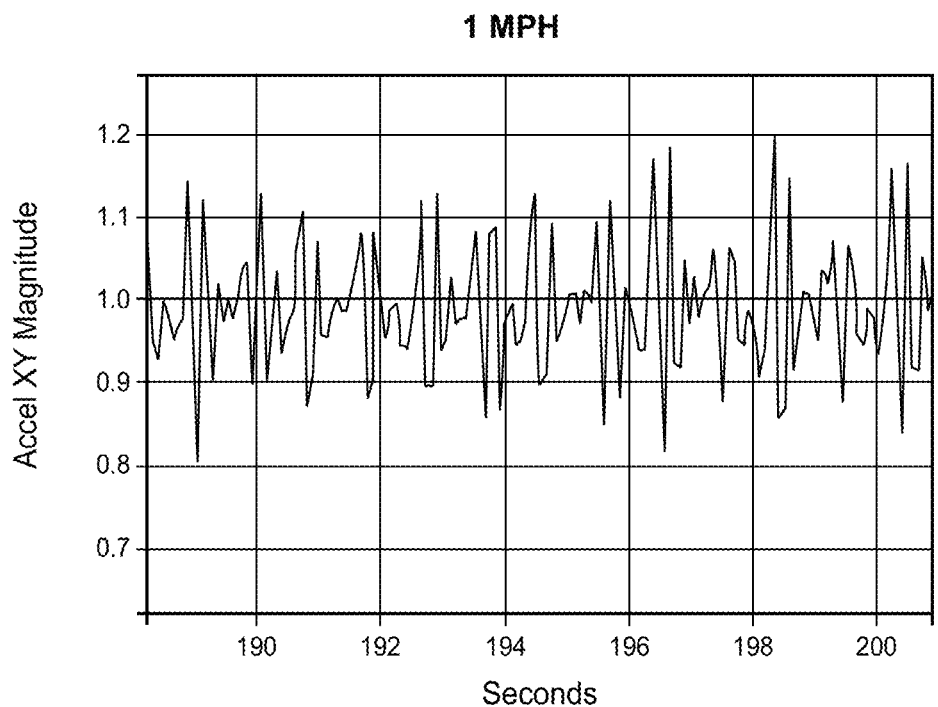
FIGS. 7A, 7B, 7C, 7D, 7E, 7F, 7G, 7H, 7I, 7J, 7K, 7L, 7M, and 7N show exemplary recorded signals for various activities in accordance with some embodiments.
Figure 7B:
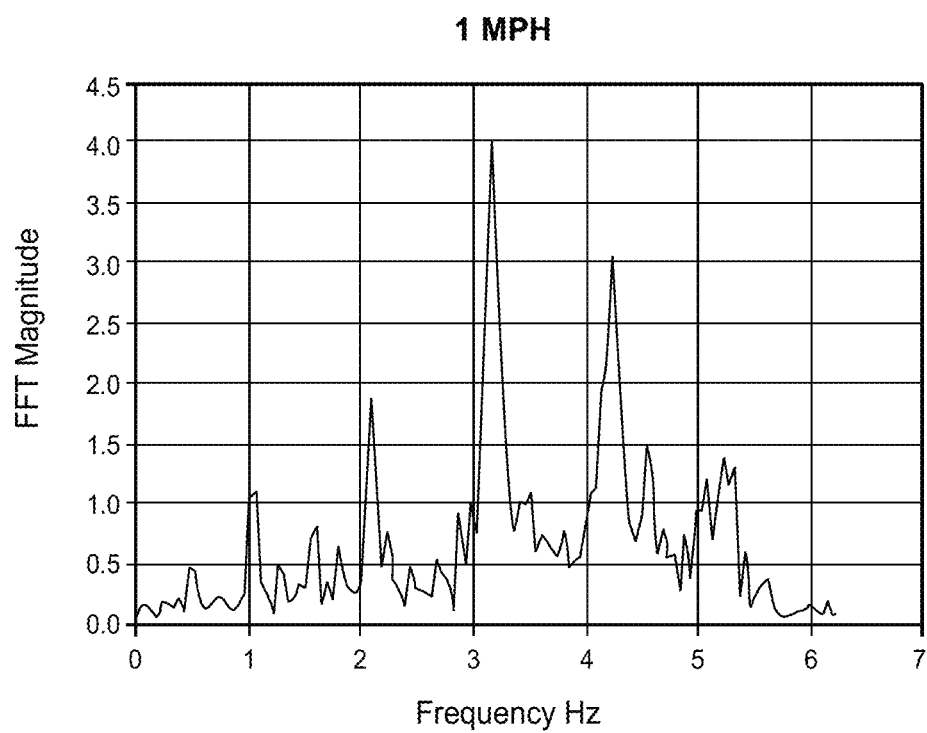
Figure 7C:
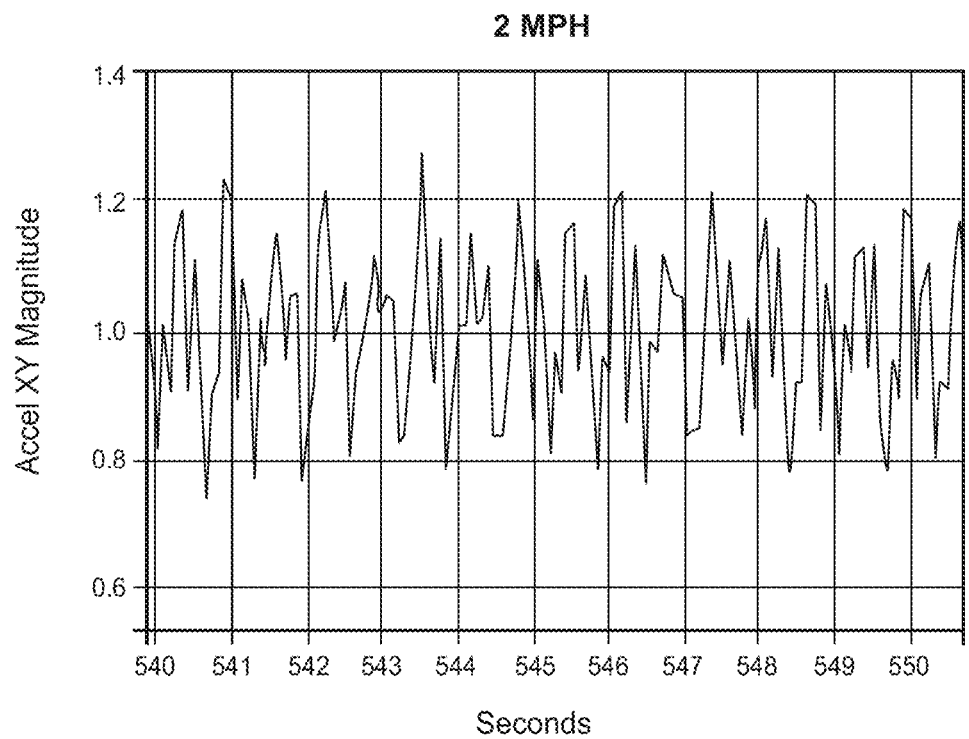
Figure 7D:
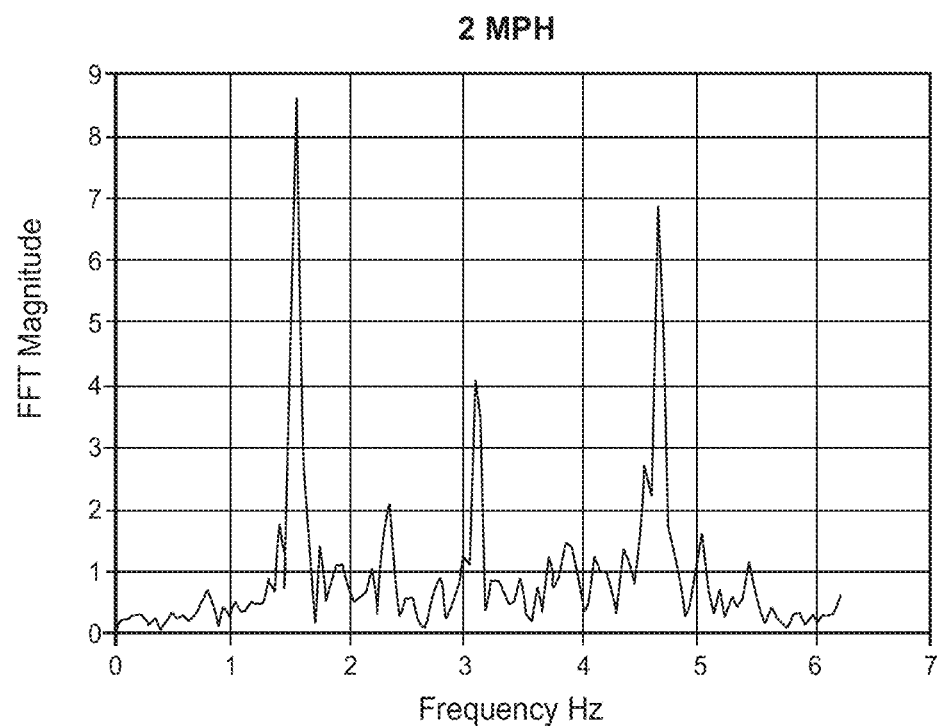
Figure 7E:
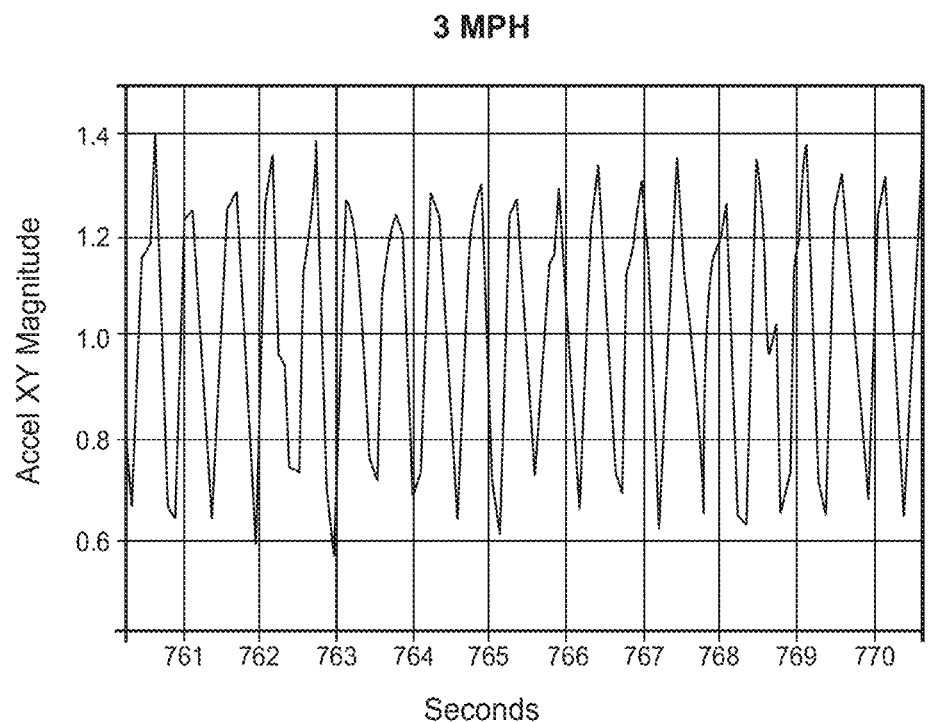
Figure 7F:
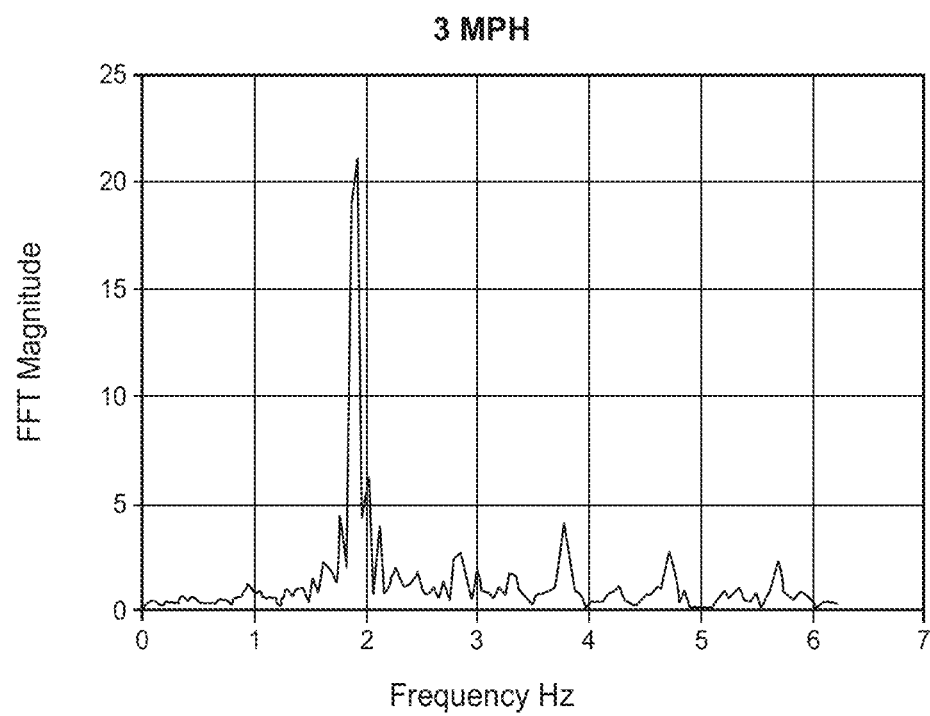
Figure 7G:
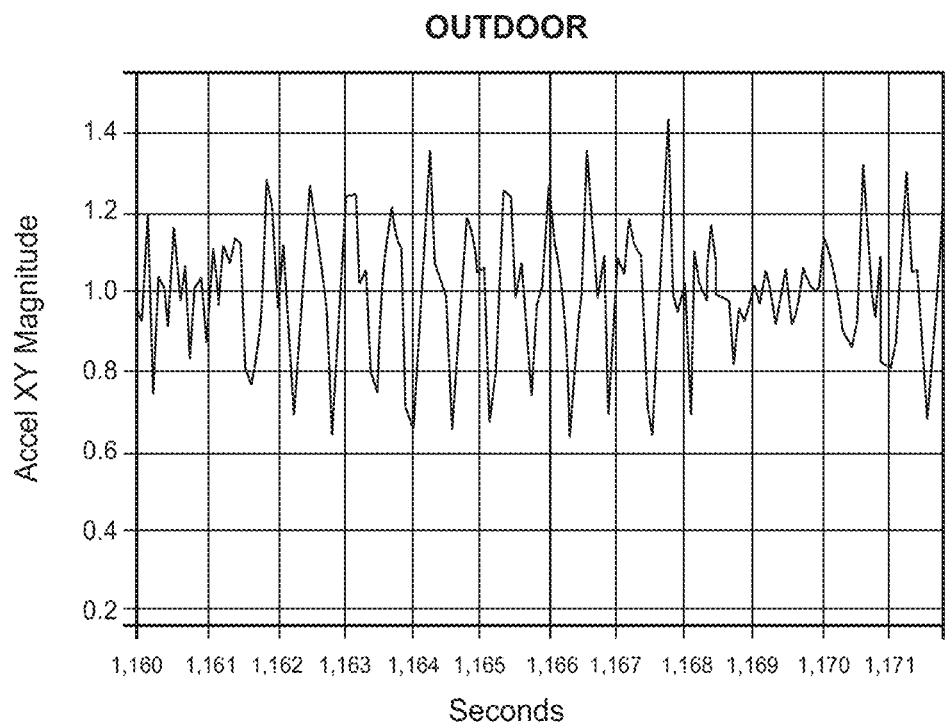
Figure 7H:
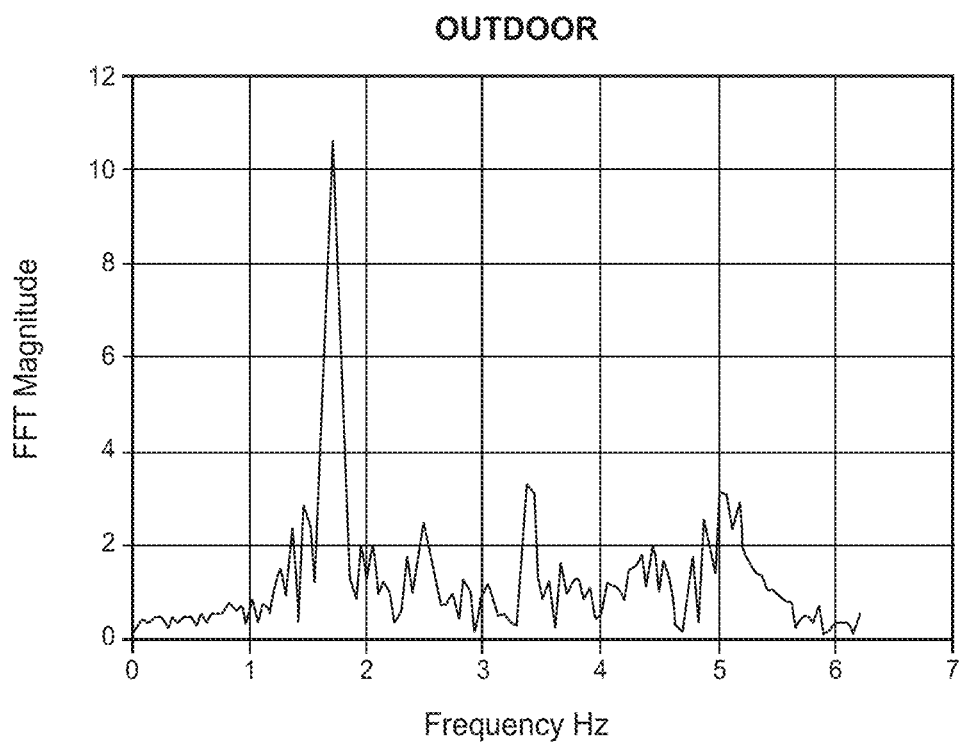
Figure 7I:
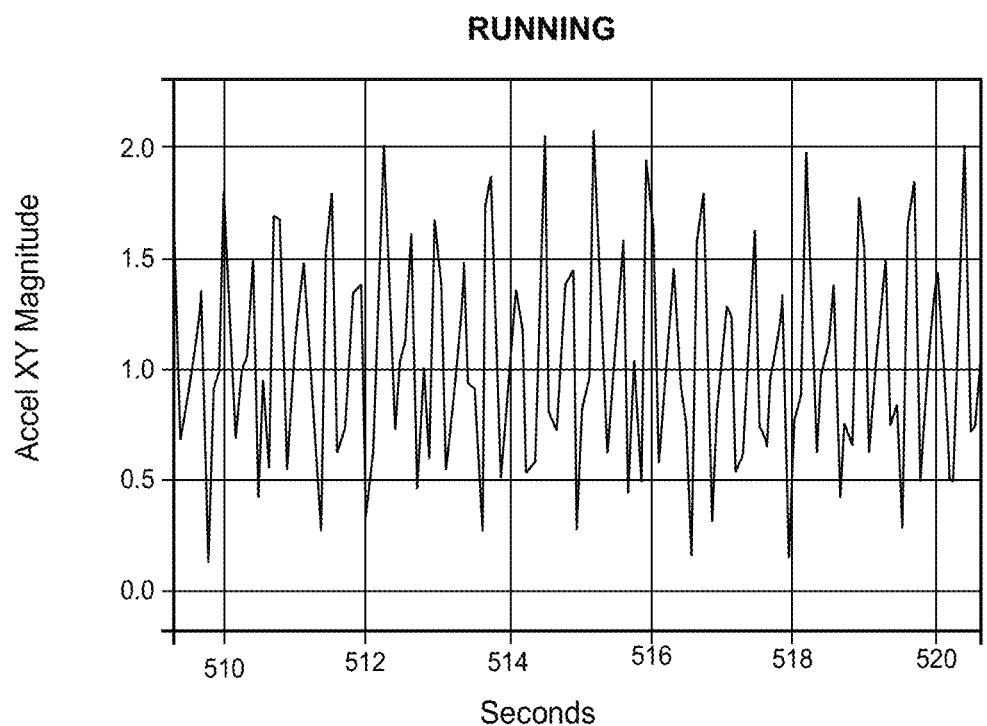
Figure 7J:
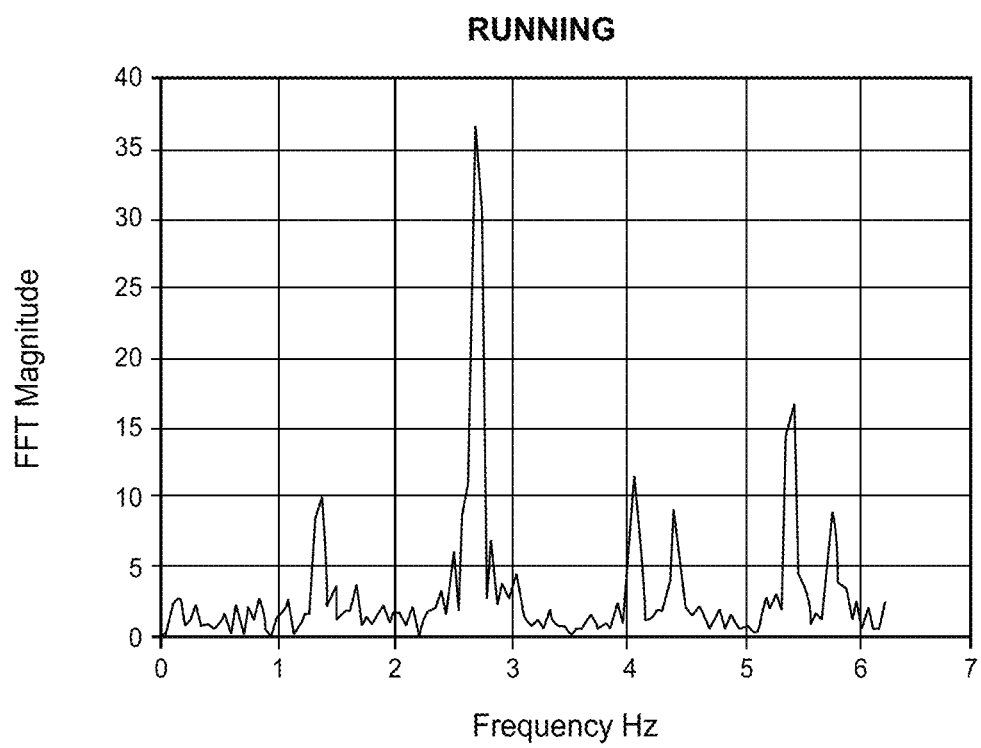
Figure 7K:
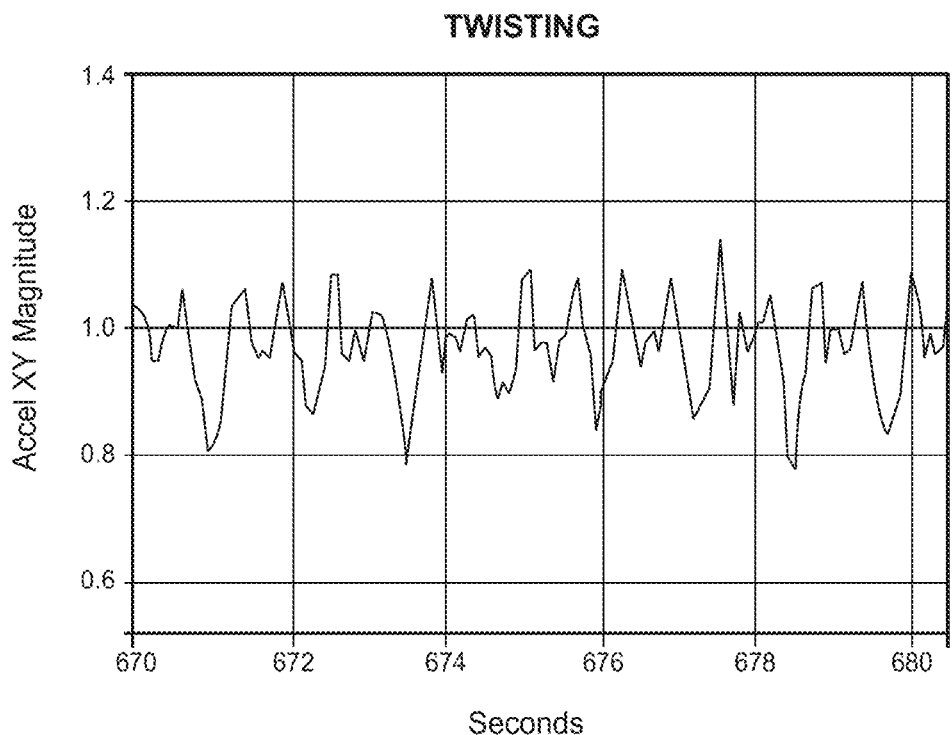
Figure 7L:
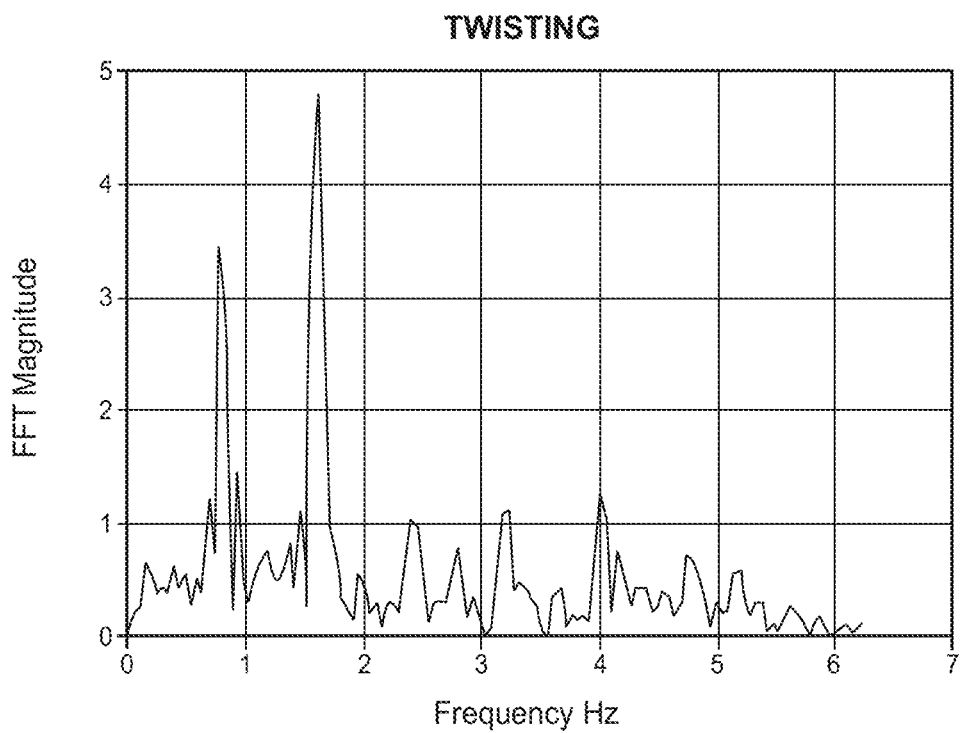
Figure 7M:
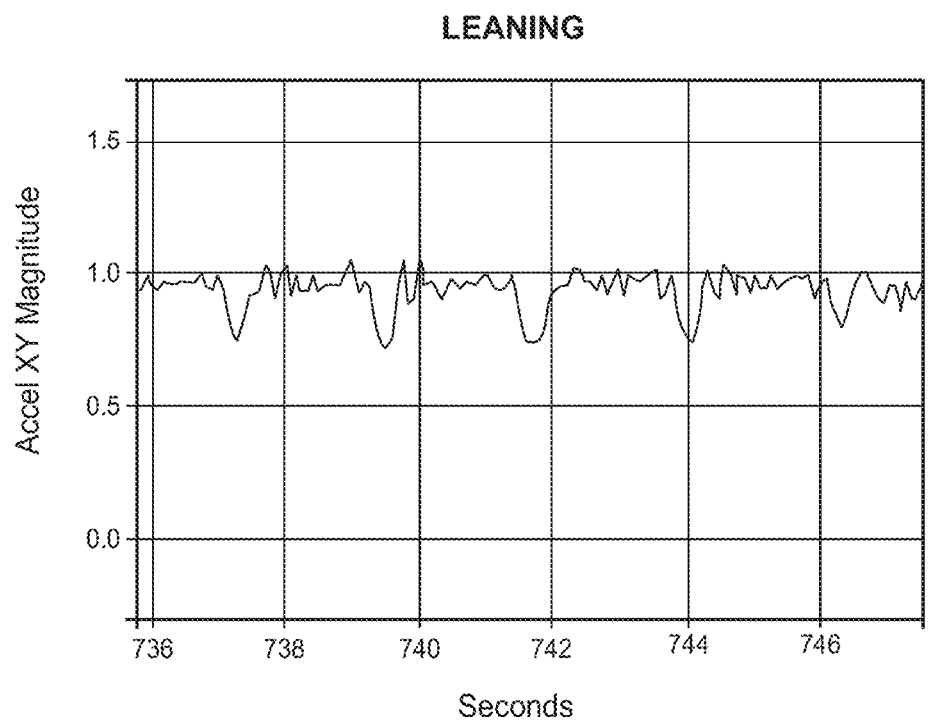
Figure 7N:
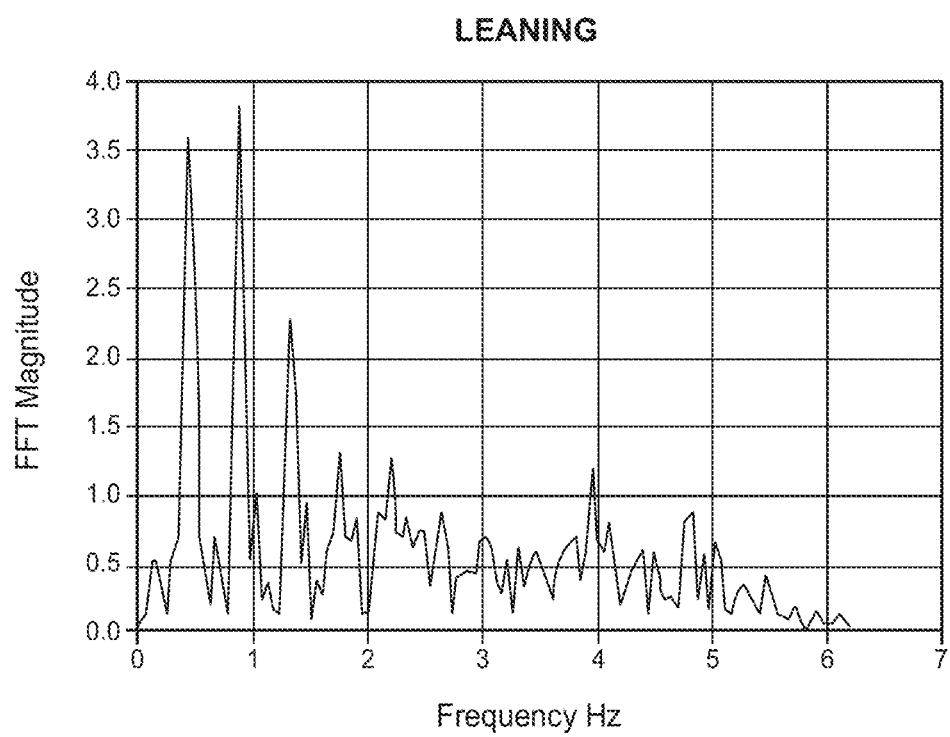

FIGS. 2, 3, and 5 are simplified flowcharts depicting processing performed for preparing or pre-processing acceleration data obtained from an accelerometer, assigning an activity class to an observation window, and counting steps according to various embodiments. The steps of FIGS. 2, 3, and 5 may be implemented in the system environment of FIG. 1, for example. As noted herein, the flowcharts of FIGS. 2, 3, and 5 illustrate the architecture, functionality, and operation of possible implementations of systems, methods, and computer program products according to various embodiments. In this regard, each block in the flowchart or block diagrams may represent a module, segment, or portion of code, which includes one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

FIG. 2 depicts a simplified flowchart 200 illustrating a process used to prepare or pre-process acceleration data obtained from the accelerometer (e.g., accelerometer 140 described with respect to FIG. 2) for use in later processing that includes a classification process used to assign an activity class to an observation window of the acceleration data, and a step counting process used to count steps within the observation window. In order for the processes of FIGS. 3 and 5 to be applied to accelerometer data obtained from an accelerometer, the accelerometer may be configured with settings to produce samples points with characteristics used by the processes. In some embodiments, a number of sample points to be employed should be specified (that is, the observation window for the spectrum) as a power of 2 (e.g., 4, 8, 16, . . . 256, 1024, . . . , etc) to better amortize computational costs during Fast Fourier Transform (FFT) operations.

For example, a sensitivity of the accelerometer may be set to +/−2 G, a sampling rate of the accelerometer may be set at 12.5 Hz, and the first in, first out (FIFO) Buffer Module may be set to streaming mode with a watermark of 128 tri-axial samples. The accelerometer may be configured to measure proper acceleration, which is the acceleration that the accelerometer experiences relative to freefall, and this is most commonly called "G-Force" (G). By way of example, an accelerometer at resting on a table will measure 1G (9.81 m/s2) straight downwards. By contrast, an accelerometer in free fall and accelerating due to the gravity of Earth will measure 0 G. The FIFO Buffer Module may be a variable-length buffer with scalable register word-width and address space, or depth, and includes a process for organizing and manipulating the data buffer, where the oldest (first) entry, or head of the queue, is processed first. A watermark is a flag, e.g., a flag for "empty", "full", "almost full", "almost empty", and "error" conditions. The depth of the flags may be adjusted. Accordingly, sampling, e.g., at 12.5 Hz, means a 5.12 second observation window can provide 64 samples, so a 64 point FFT looks at an observation window with a width of 5.12 seconds.

At step 205, acceleration data in each observation window (e.g., a 64 sample observation window) is received by the activity monitor from the accelerometer (e.g., the FIFO Buffer Module). The FIFO Buffer Module of the accelerometer may be set with a watermark to send an interrupt signal to the wake up the processor (e.g., processor 120 discussed with respect to FIG. 1) at periodic intervals such that one or more observation windows are processed successively or simultaneously. In some embodiments, the FIFO Buffer Module is set to streaming mode with a 12.5 Hz sampling rate and a FIFO watermark is set to 128 tri-axial samples (128×3 axes (X, Y, and Z)=384 of the available FIFO entries) such that the interrupt signal is sent by the FIFO Buffer Module at intervals of 128 samples, at which point two 64 sample observation windows including acceleration data for each of the axes at each sample point are received and processed successively by the processor.

At step 210, once the acceleration data is received (e.g., raw values for X, Y, and Z for each sample point) in step 205, the acceleration data is converted to Milli-G or "G-Force" (G). The accelerometer may be configured to output raw values for the acceleration data as Milli-G/least significant bit (LSB), which is the last bit on the right. Accordingly, an accelerometer set with a +/−sensitivity level of, for example 2, would provide a sensitivity total of 4 G or 4,000 Milli-Gs. In some embodiments, the raw values from the accelerometer are multiplied by the sensitivity level to convert the acceleration data to Milli-G or "G-Force" (G). For example, if the accelerometer is set to output at 16 bits, the 16 bits may be equivalent to 65,535 different readings for the range between a sensitivity of −2 G and +2 G (or −2,000 Milli-Gs and +2 Milli-Gs). Consequently, each time the LSB changes by one, the raw value changes by 0.061 (4,000 Milli-Gs/65, 535=0.061). By way of example, if the accelerometer is horizontal and at rest when using a sensitivity level of ±2 g, the raw value for the Z axis should be around 16,500. The raw value of 16,500 may then be converted by the activity monitor in step 210 by multiplying 16,500 by the LSB value for +/−2 G (e.g., 0.061) to obtain a value of 1006 Milli-Gs or 1G.

At step 215, the acceleration data in the form of Milli-G or G values calculated for the X and Y axes of each sample are combined to obtain a magnitude of acceleration for each sample. In some embodiments, equation (1) may be used to obtain the magnitude.

$$\text{magnitude} = \sqrt{x^2 + y^2}, \quad (1)$$

where X is a value of acceleration (Milli-G or G values) on the X axis and Y is a value of acceleration (Milli-G or G values) on the Y axis. At step 220, the resulting magnitudes of acceleration for the samples (e.g., 64 magnitudes for the 64 sample observation window) are normalized to be a zero mean, producing a vector X. The normalization of the acceleration data to a zero mean standardizes the range of independent variables (i.e., planarizes the acceleration data) prior to FFT transformation such that the objective functions performed thereafter will work properly.

FIG. 3 depicts a simplified flowchart 300 illustrating a process used for assigning an activity class to an observation window (e.g., a first class that includes activities associated with consecutive steps such as walking or running, and a second class that includes activities not associated with consecutive steps such as no activity or other activities than those involving a step such as jumping or swimming). For example, to improve step counter robustness of the activity monitor system, an activity classification process may be utilized in accordance with various embodiments to gate whether or not steps should be counted in a given observational window based on whether the process concludes there are consecutive step activities (versus no activity or other activities) in the window. In some embodiments, the activity classification process is implemented as a decision tree, which allows for complex non-linear partitions to be developed in the problem space based on statistical processes. However, it should be understood that the selection of characteristics to be used in the decision tree is not a statistical process, and instead is a selective process. Through this selective process it has been found surprisingly and unexpectedly that a combination of two or more of the following characteristics: (i) the L1 Difference Norm, (ii) the L2 Difference Norm, (iii) the FFT Peak Frequency, (iv) the FFT Spectral Entropy, and (iv) the FFT Total Energy, allows for the activity monitoring systems to determine a step count of a user over a predetermined period of time with minimal error rate in an environment such as a continuous glucose monitoring system with limited processing and power resources.

The generation of each characteristic for input into the activity classification process may be performed as follows in accordance with various embodiments. At step 305, a sum is taken of absolute differences of magnitudes (e.g., the jerk) of acceleration calculated for each sample in step 215 of FIG. 2. In some embodiments, equation (3) may be used to obtain the sum of absolute differences of magnitudes of acceleration.

$$L1 \text{ Difference norm} = \Sigma_{i=0}^{63} \text{abs}(X_{i+1} - X_i) \quad (3),$$

where X is the vector X of the magnitudes of acceleration calculated in step 220 of FIG. 2. The LI Difference Norm effectively measures an amount of change (i.e., amplitude) of the signal, which correlates well with both the presence of steps and the speed of the steps (via acceleration magnitude).

At step 310, a sum is taken of absolute second differences of magnitudes (e.g., the jounce) of acceleration calculated for each sample in step 215 of FIG. 2. In some embodiments, equation (4) may be used to obtain the sum of absolute second differences of magnitudes of acceleration.

$$L2 \text{ Difference norm} = \Sigma_{i=0}^{62} \text{abs}((X_{i+2} - X_{i+1}) - (X_{i+1} - X_i)) = \Sigma_{i=0}^{62} \text{abs}(X_{i+2} - 2X_{i+1} + X_i) \quad (4),$$

where X is the vector X of the magnitudes of acceleration calculated in step 220 of FIG. 2. The L2 Difference Norm effectively measures a similarity, a quality, or a correlation between two signals, which correlates well with the presence of continuous steps.

At step 315, the FFT is calculated for the vector X of the magnitudes of acceleration calculated in step 220 of FIG. 2 (e.g., FFT size=64). The FFT is a known method for calculating the Discrete Fourier Transform (DFT), and is not addressed in detail herein. At step 320, a peak frequency in Hz corresponding to a maximum energy in the computed FFT is determined. In some embodiments, equation (5) may be used to obtain the peak frequency.

$$\text{FFT Peak Freq} = \mathrm{argmax}(P(f_i)) \quad (5),$$

where argmax is the x-axis value at which the function's y-axis value is at its max (e.g., frequency at which $P(f_i)$ is at its max value), $P(f_i)$ is the FFT function indexed by frequency ($f_i$). The integration of the peak frequency over the observation window corresponds to the number of steps in the observation window, assuming a constant walking/running speed.

At step 325, spectral entropy in the computed FFT is determined. In some embodiments, equation (6) may be used to obtain the spectral entropy.

$$\text{FFT Spectral Entropy} = \Sigma - P(f_i) * \log(P(f_i)) \quad (6),$$

where $P(f_i)$ is the FFT function indexed by frequency ($f_i$). A clean activity single such as a walking/running signal will have very little entropy in the FFT (there will be only a single large frequency peak). However, entropy in the FFT may vary at different walking/running speeds due to unmodeled dynamics of human motion. Consequently, spectral entropy presents as a good metric for differentiation.

At step 330, a total energy in the computed FFT is determined. In some embodiments, equation (7) may be used to obtain the total energy.

$$\text{FFT Total Energy} = \Sigma P(f_i)) \quad (7),$$

where $P(f_i)$ is the FFT function indexed by frequency ($f_i$). A clean activity single such as a walking/running signal will exhibit most of its energy in the FFT at a corresponding dominant peak frequency. However, energy in the FFT may vary at different walking/running speeds due to unmodeled dynamics of human motion. Thus, energy also presents as a good metric for differentiation.

A combination of characteristics including two or more of the following characteristics: (i) the L1 Difference Norm, (ii) the L2 Difference Norm, (iii) the FFT Peak Frequency, (iv) the FFT Spectral Entropy, and (iv) the FFT Total Energy, are input into the activity classification process at step 335, which determines activity occurring within the observation window (e.g., a 64 sample observation window) and assigns an activity class to the observation window based on the determined activity. In some embodiments, each of the two or more characteristics is selected without replication from the group consisting of: (i) the L1 Difference Norm, (ii) the L2 Difference Norm, (iii) the FFT Peak Frequency, (iv) the FFT Spectral Entropy, and (iv) the FFT Total Energy. In alternative embodiments, the characteristics include the L1 Difference Norm and the FFT Spectral Entropy. In other embodiments, the characteristics include the L1 Difference Norm, the L2 Difference Norm, the FFT Peak Frequency, and the FFT Spectral Entropy. In yet other embodiments, the characteristics include the L1 Difference Norm, the L2 Difference Norm, the FFT Peak Frequency, the FFT Spectral Entropy, and the FFT Total Energy.

In various embodiments, the activity classification process for determining activity occurring within the observation window and assigning an activity class to the observation window includes: (i) determining a probability for each of one or more activities determined to be occurring with the observation window, (ii) determining an activity with the greatest probability of occurring within the observation window based on the determined probabilities for the one or more activities, (iii) assigning a first class to the observation window when the determined activity is associated with consecutive steps, and (iv) assigning a second class to the observation window when the determined activity is not associated with consecutive steps. In some embodiments, the one or more activities includes no activity, activity other than those including steps (e.g., jumping or swimming), walking, jogging, running, etc., the first class may include activities associated with consecutive steps such as walking or running, and the second class may include activities not associated with consecutive steps such as no activity or other activities than those involving a step.

In other embodiments, the first class may be partitioned to provide greater detail concerning the frequency in which the consecutive steps are being taken. For example, the first class may instead be separated into a combination of a low activity class (a lower frequency of consecutive steps being taken such as in walking) and a high activity class (a higher frequency of consecutive steps being taken such as in jogging/running). The low activity class may be defined as approximately a 1.5-3 mph walk, the high activity class may be defined as approximately 3-7 mph jog/run, and the second class, no activity class, or other activity class may be defined as anything less than approximately 1.5 mph activity. In such an instance the activity classification process for determining activity occurring within the observation window and assigning an activity class to the observation window may include: (i) determining a probability for each of one or more activities determined to be occurring with the observation window, (ii) determining an activity with the greatest probability of occurring within the observation window based on the determined probabilities for the one or more activities, (iii) assigning a first class to the observation window when the determined activity is associated with walking, (iv) assigning a second class to the observation window when the determined activity is associated with running, and (iv) assigning a third class to the observation window when the determined activity is associated with no activity or an activity that does not include consecutive steps.

Figure 4:
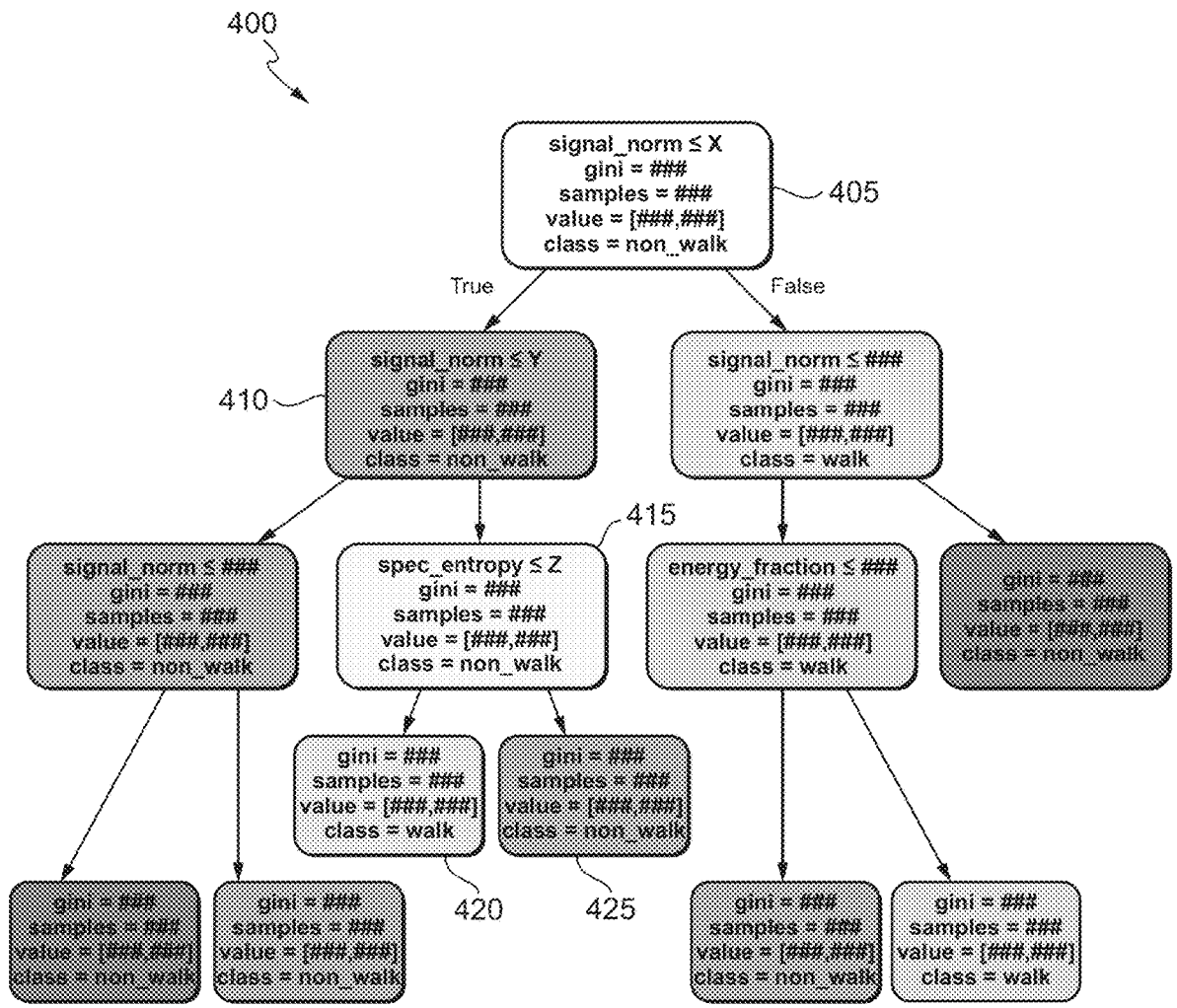
FIG. 4 shows an illustrative decision tree implemented in accordance with some embodiments.

In various embodiments, the activity classification process includes the use of a decision tree developed statistically through machine learning on accelerometer training data to determine activity occurring within the observation window and assign an activity class to the observation window. An example of a simple decision tree used in the activity classification process is shown in FIG. 4; however it should be understood that the decision tree used in actual practice may be more complex (e.g., the decision tree may further include branches to determine additional activity classes such as high activity or running). The left branch may be traversed when the decision tree element inequality is satisfied and the right branch may be traversed when the decision tree element inequality is not satisfied. The node shading indicates the nodal decision strength for non-walking and walking. The leaf nodes do not have any conditions, as they are the final class "decision" of the tree.

As an illustrative example, if the LI Difference Norm calculated for an observation window is less than or equal to "X" in step 405 and greater than "Y" in step 410, then the spectral entropy calculated for the observation window is compared to a value "Z" in step 415. If the spectral entropy is less than or equal to "Z", then in step 420 a probability is assigned to the activity of walking based on the nodal decision strength for the leaf. If the spectral entropy is greater than "Z", then in step 425 a probability is assigned to the activity of non-walking based on the nodal decision strength for the leaf. The activity (e.g., non-walking or walking) with the greatest probability of occurring within the observation window is then determined based on the determined probabilities for the one or more activities. The observation window is then assigned a class based on the activity determined to have the greatest probability of occurring within the observation window (e.g., a low activity class may be assigned to the observation window if the activity having the greatest probability of occurring was walking).

At step 340, the activity class determined in step 335 is used to increment a total count of the activity class for a user over a predetermined period of time. In some embodiments, a record is maintained in a database (e.g., database 160 as discussed with respect to FIG. 1) for each activity class (e.g., first class, second class, third class, no activity class, low activity class, high activity class, etc.), and the total count for each activity class is incremented (e.g., incremented by 1) each time the activity class is assigned to an observation window. Accordingly, the activity monitor is configured to keep a tally of all types of activity performed by a user over a predetermined period of time (e.g., an hour, a day, a week, etc.).

FIG. 5 depicts a simplified flowchart 500 illustrating a step counting process used to count steps within an observation window. At step 505, a determination is made as to whether the step counting process should be initiated. If the activity classification process (e.g., step 335 described with respect to FIG. 3) concludes that the activity class assigned to the observation window is associated with no activity or other activities than those involving a step (e.g., jumping or swimming), then it is determined that consecutive steps are not present in the activity and consequently the process ends at step 510 and the step counting process is not performed for the observation window. If the activity classification process concludes that the activity class assigned to the observation window is associated with a low activity (e.g., walking) and/or a high activity (e.g., running), then it is determined that consecutive steps are present in the activity and consequently further processing is performed starting at step 515 to determine an estimate of the number of consecutive steps present in the observation window.

At step 515, harmonics introduced into the accelerometer data are detected and adjusted by scaling the magnitude of the FFT to accurately count consecutive steps despite the harmonics. The FFT may be obtained from step 315 described with respect to FIG. 3. The harmonics or higher order effects may be associated with various motions or noises (e.g., associated with attachment of the continuous glucose monitor to a user's body) that have a frequency that is an integer multiple of the fundamental frequency or frequency associated with consecutive steps for an activity class (e.g., a low activity class or a high activity class). In certain embodiments, the process of detecting and adjusting for the harmonics may include selecting a binary spectrum weight function based on the activity class determined for the observation window. The binary spectrum weight enables the step counting process to accurately remove the harmonics in the spectrum domain, and thus correctly identify the spectral peak or fundamental frequency that represents the number of consecutive steps per second within the observed time window. For example, equation (8) may be used to scale the magnitude of the FFT if a low activity class is assigned to the observation window, and equation (9) may be used to scale the magnitude of the FFT if a high activity class is assigned to the observation window.

$$M'=M, f \leq 1 \text{ Hz}$$

$$M'=M/f^2, f>1 \text{ Hz} \tag{8}$$

$$M'=M, f \leq 3 \text{ Hz}$$

$$M'=M/f^2, f>3 \text{ Hz} \tag{9}$$

where M is magnitude and f is the FFT frequency. In some embodiments, $1/f^2$ is implemented as a lookup table to optimize runtime. This scaling dampens the harmonics and higher order effects that may be present in the FFT. The window of scaling corresponds to the expected frequency range for steps for each activity class.

At step 520, a peak frequency in Hz corresponding to a maximum energy in the computed FFT is determined using the scaled magnitude calculated in step 515. In some embodiments, equation (10) may be used to obtain the peak frequency.

$$\text{Modified FFT Peak Freq}=\text{argmax}(P(f_i)) \tag{10}$$

where argmax is the x-axis value at which the function's y-axis value is at its max (e.g., frequency at which $P(f_i)$ is at its max value), $P(f_i)$ is the FFT function indexed by frequency ($f_i$). The dominant peak frequency corresponds to the walking frequency in Hz.

At step 525, the step count of the observation window is determined by integrating the dominant peak frequency by the width of the observation window. In some embodiments, equation (11) may be used to increment the step count.

$$\text{Step Count}=\text{Modified FFT Peak Freq}*\text{width} \tag{11}$$

where Modified FFT Peak Freq is calculated in step 520 and width is the width of the observation window (e.g., the width of the observation window may be 5.12 seconds for the 64 sample observation window).

At step 530, the step count determined in step 525 is used to increment the total step count for the user over a predetermined period of time. In some embodiments, a record is maintained in a database (e.g., database 160 as discussed with respect to FIG. 1) for the total step count (e.g., the step count over multiple observation windows throughout a predetermined period time), and the total step count is incremented (e.g., increment by the steps determined in step 520) each time an observation window in processed. In other embodiments, since the activity monitoring system determines a class of activity being performed (e.g., walking or running), a separate tally may be kept for steps associated with each class of activity. Accordingly, the activity monitor is configured to keep a tally of all steps taken by a user over a predetermined period of time (e.g., a half hour, an hour, a day, a week, etc.).

In various embodiments, the activity class data and the step count data maintained in a database (e.g., database 160 as discussed with respect to FIG. 1) are used by the continuous glucose monitoring system to provide contextual labels to glucose readings prior to reporting the glucose readings. For example, the continuous glucose monitoring system may be configured to perform glucose analysis on a patient (e.g., determine a patient's blood glucose concentration) and report glucose readings based on a time schedule (e.g., a predetermined period of time such as a half hour). Prior to reporting the glucose readings to a mobile device/reader, the continuous glucose monitoring system may be further configured to review the database and provide contextual labels (e.g., "high activity time interval" vs. "low activity interval" vs. "no activity interval") to the glucose readings based on the activity class data and the step count data recorded for the observation windows that occurred within the predetermined period of time (e.g., the previous half hour).

In additional or alternative embodiments, the activity class data and the step count data maintained in a database (e.g., database 160 as discussed with respect to FIG. 1) are used by the continuous glucose monitoring system to calibrate or correct glucose readings prior to reporting the glucose readings. For example, the continuous glucose monitoring system may be configured to perform glucose analysis on a patient (e.g., determine a patient's blood glucose concentration) and report glucose readings based on a time schedule (e.g., a predetermined period of time such as a half hour). Prior to reporting the glucose readings to a mobile device/reader, the continuous glucose monitoring system may be further configured to review the database and calibrate or correct the glucose readings based on the activity class data and the step count data recorded for the observation windows that occurred within the predetermined period of time (e.g., the previous half hour). In some embodiments, the calibrating or correcting the glucose readings may include applying a correction factor to the glucose reading based on the activity class data and the step count data recorded for the observation windows that occurred within the predetermined period of time (e.g., the previous half hour).

In additional or alternative embodiments, the activity class data and the step count data maintained in a database (e.g., database 160 as discussed with respect to FIG. 1) are used by the continuous glucose monitoring system to report predetermined time period based metrics. For example, the continuous glucose monitoring system may be configured to report walking minutes and running minutes based on a time schedule (e.g., a predetermined period of time such as daily) since the activity monitor is configured to maintain data on whether an individual is walking or running and the steps associated with each activity class.

IV. Examples

Without intending to limit the scope of the embodiments discussed herein, the systems and methods implemented in various embodiments may be better understood by referring to the following examples.

Example 1 (Activity Monitoring System—Power Usage)

An ADXL362 accelerometer was configured with the following settings to produce characteristics used in the processes described herein to assign an activity class to an observation window and count steps: +/−2 G operating mode, 12.5 Hz sampling rate, normal noise mode, FIFO set to streaming mode, and a FIFO watermark set to 128 tri-axial samples. An investigation of the activity monitoring system during runtime revealed that the activity monitoring system increases power draw from the environment in which it is operating in the following areas: (i) accelerometer base load, which is a continuous power draw by the ADXL362 accelerometer when it is sampling, (ii) FIFO data download, which is the system power used to download 128 samples from the accelerometer FIFO, (iii) activity classification algorithm and step counting algorithm, which is system power used to run the algorithms, and (iv) record to database, which is system power required to log classification and step count to database at intervals (this power draw is trivial and was thus ignored in this example).

With the given accelerometer configuration and at a nominal operating voltage of 3.2 V, the accelerometer base load draw was a constant average power draw of 1.8 µA. The FIFO data download step includes processing data that consists of 776 bytes of data being transferred between the processor and accelerometer, including: 4 bytes to read the number of samples in the FIFO (command, address, and u16 data), 768 bytes=128 samples×6 bytes per sample, and 4 bytes=1 byte overhead per 42 samples as read facilitated in chunks of bytes. At an operating rate of 8 MHZ, the download step will take at least 0.776 ms. In practice, this step takes 1.375 ms of CPU uptime including overheads, with a system power draw of 3.65 mA. Given the FIFO should be downloaded every 10.24 s, this uptime corresponds to an average power draw of 0.49 µA. Running the activity classification algorithm and the step counting algorithm on the 128 byte of data (two 64-sample observation windows) utilizes a CPU uptime of 1.806 ms (empirical). This uptime corresponds to an average power draw of 0.64 µA. Accordingly, the activity monitoring system adds an average power draw of 2.93 µA to the average system power draw at a nominal operating voltage of 3.2 V.

In contrast, the conventional activity monitoring system adds an average power draw of 8.48 µA to the average system power draw at a nominal operating voltage of 3.2 V. The only difference between the activity monitoring systems being the algorithms used for determining the step count. Consequently, the processes of various embodiments discussed herein are capable of reducing the power draw on the environment in which the activity monitoring system is operating by about 5.5 µA. Advantageously, these approaches provide activity monitoring systems and methods that are capable of operating in an environment such as a continuous glucose monitoring system with limited processing and power resources.

Example 2 (Activity Monitoring System—Error Rate Verification)

Figure 8A:
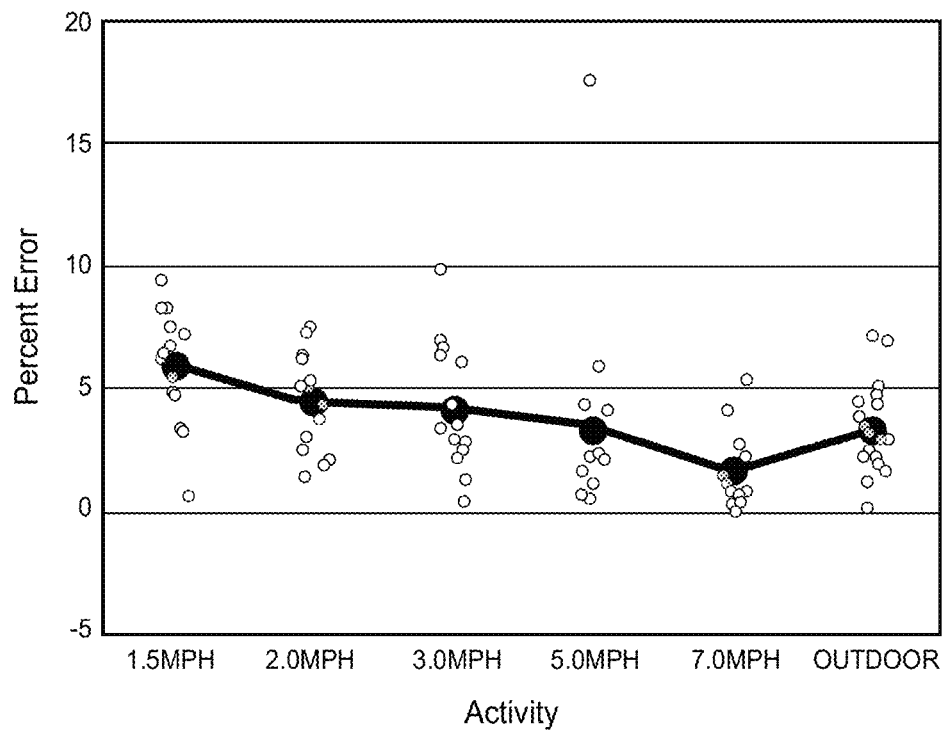
FIGS. 8A and 8B show error rate in step counting in accordance with some embodiments.
Figure 8B:
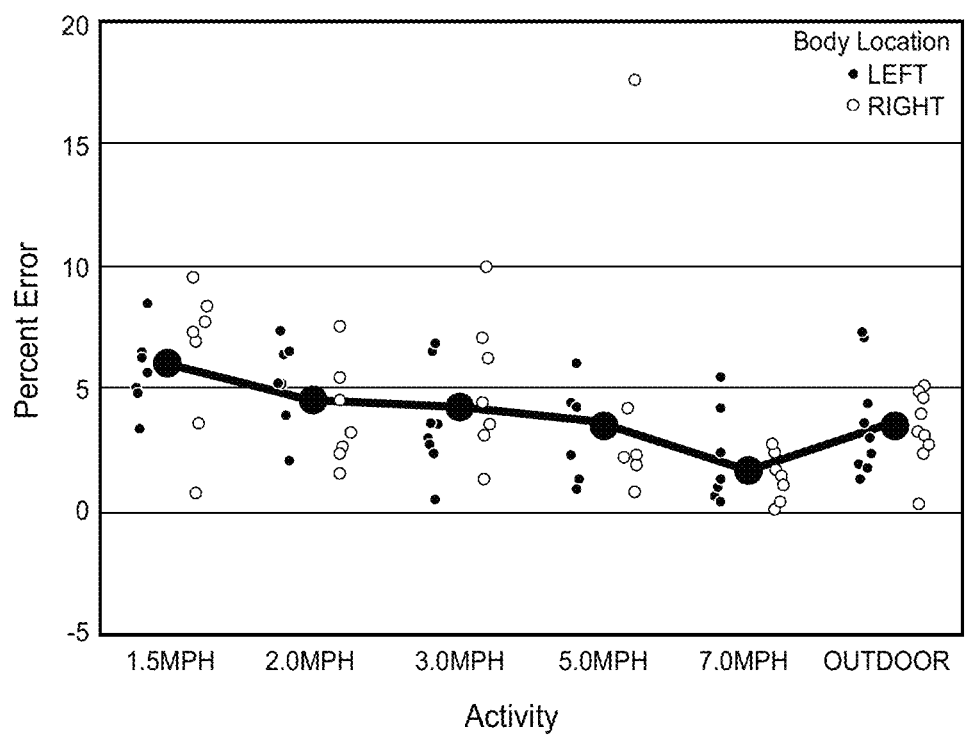

The accelerometer and activity monitoring system described with respect to Example 1 were attached to 10 participants. In particular, one accelerometer and activity monitoring system was attached to the right abdomen of each participant and a raw data logger (activity monitoring system used as a control/training) was attached to the right abdomen of each participant. The activity monitoring systems and data loggers were set to record accumulated consecutive steps every 15 seconds, and an experimenter manually counted actual consecutive steps using a clicker (+/−1 step error). The participants were each asked to perform various activities indoors (i.e., on a treadmill) and outdoors for various lengths of time (as shown in FIG. 6). FIGS. 7A, 7B, 7C, 7D, 7E, 7F, 7G, 7H, 7I, 7J, 7K, 7L, 7M, and 7N show signals generated and recorded for each of the activities performed by the participants, in accordance with various embodiments. FIGS. 8A and 8B show that for each activity the error in determining the step count was less than 10%, and less than 5% for any activity having a speed of greater than 1.5 mph. Accordingly, the activity monitoring system is capable of maintaining an error rate of less than 10% for activities that include taking consecutive steps such as walking, jogging, and running no matter whether the activity is performed on a treadmill or outdoors.

In contrast, the conventional activity monitoring system is capable of maintaining an error rate of less than 10% for activities that include taking consecutive steps such as walking, jogging, and running outdoors but demonstrate high error rate (e.g., up to 60% error rate) for determining steps taken during certain physical activities such as walking on a treadmill. Consequently, the processes of the various embodiments discussed herein are capable of achieving minimal error in step count, and in some circumstances even improve upon conventional step count techniques. Advantageously, these approaches provide activity monitoring systems and methods that are capable of determining user activity with minimal error rate while operating in an environment such as a continuous glucose monitoring system with limited processing and power resources.

While various embodiments have been described in detail, modifications within the spirit and scope of the present invention will be readily apparent to the skilled artisan. It should be understood that certain aspects and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the present invention.

What is claimed is:

1. A system comprising:
    one or more processors; and
    a memory coupled to the one or more processors, the memory storing one or more instructions that, when executed by the one or more processors, cause the one or more processors to perform a process including:
    obtaining, by the one or more processors, acceleration data for observation windows to detect movement of a user, wherein the acceleration data is sensed by an accelerometer;
    determining, by the one or more processors, two or more characteristics of the acceleration data obtained for each observation window, wherein the two or more characteristics include at least a frequency domain characteristic; and
    for an observation window among the observation windows:
    inputting, by the one or more processors into a decision tree algorithm stored in the memory, the two or more characteristics corresponding to the observation window, to determine whether the movement of the user includes taking consecutive steps within the observation window,
        upon the determining by the decision tree algorithm that the movement of the user includes taking the consecutive steps, determining, by the one or more processors, a peak frequency based on the two or more characteristics corresponding to the observation window, and
        determining, by the one or more processors, a step count for the observation window by integrating the peak frequency in the observation window over a width of the observation window,
    wherein the process further includes outputting, by the one or more processors, information related to the step count to an external device.

2. The system of claim 1, wherein the process further includes:
    determining, by the decision tree algorithm, among one or more activities occurring within the observation window, an activity with a greatest probability of occurring within the observation window, wherein the determining the activity with the greatest probability of occurring includes determining that the activity with the greatest probability of occurring is a type of activity associated with the consecutive steps;
    in response to determining that the activity with the greatest probability of occurring is the type of activity associated with the consecutive steps, assigning a first class to the observation window; and
    determining, by the decision tree algorithm, another probability respectively for one or more other activities determined to be occurring within the observation window based on the two or more characteristics.

3. The system of claim 2, wherein the one or more activities include activities associated with the consecutive steps and activities not associated with the consecutive steps.

4. The system of claim 2, wherein the process further includes:
    determining two or more characteristics of additional acceleration data obtained for another observation window;
    determining, by the decision tree algorithm, a probability respectively for the one or more activities determined to be occurring within the another observation window based on the two or more characteristics of the additional acceleration data;
    determining, among the one or more activities determined to be occurring within the another observation window and by the decision tree algorithm, an activity with the greatest probability of occurring within the another observation window based on the probability respectively determined for the one or more activities, wherein the determining the activity with the greatest probability of occurring includes determining that the activity with the greatest probability of occurring is a type of activity not associated with the consecutive steps;
    in response to determining that the activity with the greatest probability of occurring is the type of activity not associated with the consecutive steps, assigning a second class to the observation window; and
    incrementing a count of the second class in a database and stopping processing of the additional acceleration data for the another observation window without determining a step count for the another observation window.

5. The system of claim 4, wherein the first class corresponds to low activity or high activity, and the second class corresponds to no activity.

6. The system of claim 2, wherein the process further includes incrementing a count of the first class in a database and adding the step count for the observation window to a total step count stored in the database.

7. The system of claim 6, wherein the process further includes reporting a glucose reading with a contextual label based on the count of the first class and the total step count in the database.

8. The system of claim 6, wherein the process further includes correcting a glucose reading based on the count of the first class and the total step count in the database.

9. A non-transitory computer readable storage medium storing one or more instructions that, when executed by one or more processors of a computing system, cause the computing system to perform operations including:

obtaining, by the one or more processors, acceleration data for observation windows to detect movement of a user, wherein the acceleration data is sensed by an accelerometer;

determining, by the one or more processors, two or more characteristics of the acceleration data obtained for each observation window, wherein the two or more characteristics include at least a frequency domain characteristic; and for an observation window among the observation windows:

inputting, by the one or more processors into a decision tree algorithm stored in a memory, the two or more characteristics corresponding to the observation window, to determine whether the movement of the user includes taking consecutive steps within the observation window, and upon the determining by the decision tree algorithm that the movement of the user includes taking the consecutive steps, determining, by the one or more processors, a step count for the observation window as a product of a peak frequency in the observation window and a width of the observation window, wherein the process further includes outputting, by the one or more processors, information related to the step count to an external device.

10. The non-transitory computer readable storage medium of claim 9, wherein the operations further include:

determining, by the decision tree algorithm, among one or more activities occurring within the observation window, an activity with a greatest probability of occurring within the observation window, wherein the determining the activity with the greatest probability of occurring includes determining that the activity with the greatest probability of occurring is a type of activity associated with the consecutive steps;

in response to determining that the activity with the greatest probability of occurring is the type of activity associated with the consecutive steps, assigning a first class to the observation window; and determining, by the decision tree algorithm, another probability respectively for one or more other activities determined to be occurring within the observation window based on the two or more characteristics.

11. The non-transitory computer readable storage medium of claim 10, wherein the one or more activities include no activity.

12. The non-transitory computer readable storage medium of claim 10, wherein the operations further includes:

determining two or more characteristics of additional acceleration data obtained for another observation window;

determining, by the decision tree algorithm, a probability respectively for the one or more activities determined to be occurring within the another observation window based on the two or more characteristics of the additional acceleration data;

determining, among the one or more activities determined to be occurring within the another observation window and by the decision tree algorithm, an activity with the greatest probability of occurring within the another observation window based on the probability respectively determined for the one or more activities, wherein the determining the activity with the greatest probability of occurring includes determining that the activity with the greatest probability of occurring is a type of activity not associated with the consecutive steps;

in response to determining that the activity with the greatest probability of occurring is the type of activity not associated with the consecutive steps, assigning a second class to the observation window; and incrementing a count of the second class in a database and stopping processing of the additional acceleration data for the another observation window without determining a step count for the another observation window.

13. The non-transitory computer readable storage medium of claim 12, wherein the first class corresponds to low activity or high activity, and the second class corresponds to no activity.

14. The non-transitory computer readable storage medium of claim 10, wherein the operations further include incrementing a count of the first class in a database and adding the step count for the observation window to a total step count stored in the database.

15. The non-transitory computer readable storage medium of claim 14, wherein the operations further include reporting a glucose reading with a contextual label based on the count of the first class and the total step count in the database.

16. The non-transitory computer readable storage medium of claim 14, wherein the operations further include correcting a glucose reading based on the count of the first class and the total step count in the database.

17. A method comprising:

obtaining, by one or more processors, acceleration data for observation windows to detect movement of a user, wherein the acceleration data is sensed by an accelerometer;

determining, by the one or more processors, two or more characteristics of the acceleration data obtained for each observation window, wherein the two or more characteristics include at least a frequency domain characteristic; and for an observation window among the observation windows:

inputting, by the one or more processors into a decision tree algorithm stored in a memory, the two or more characteristics corresponding to the observation window, to determine whether the movement of the user includes taking consecutive steps within the observation window, upon the determining by the decision tree algorithm that the movement of the user includes taking the consecutive steps, determining, by the one or more processors, a peak frequency based on the two or more characteristics corresponding to the observation window, and determining, by the one or more processors, a step count for the observation window as a product of the peak frequency in the observation window and a width of the observation window, wherein the process further includes outputting, by the one or more processors, information related to the step count to an external device.

18. The method of claim 17, further comprising:

determining, by the decision tree algorithm, among one or more activities occurring within the observation window, an activity with a greatest probability of occurring within the observation window, wherein the determining the activity with the greatest probability of occurring includes determining that the activity with the greatest probability of occurring is a type of activity associated with the consecutive steps;

in response to determining that the activity with the greatest probability of occurring is the type of activity associated with the consecutive steps, assigning, by the one or more processors, a first class to the observation window; and determining, by the decision tree algorithm, another probability respectively for one or more other activities determined to be occurring within the observation window based on the two or more characteristics.

19. The method of claim 18, wherein the one or more activities include no activity.

20. The method of claim 17, further comprising:

determining, by the one or more processors, two or more characteristics of additional acceleration data obtained for another observation window;

determining, by the decision tree algorithm, a probability respectively for one or more activities determined to be occurring within the another observation window based on the two or more characteristics of the additional acceleration data;

determining, among the one or more activities determined to be occurring within the another observation window and by the decision tree algorithm, an activity with a greatest probability of occurring within the another observation window based on the probability respectively determined for the one or more activities, wherein the determining the activity with the greatest probability of occurring includes determining that the activity with the greatest probability of occurring is a type of activity not associated with the consecutive steps;

in response to determining that the activity with the greatest probability of occurring is the type of activity not associated with the consecutive steps, assigning, by the one or more processors, a second class to the observation window; and incrementing, by the one or more processors, a count of the second class in a database and stopping processing of the additional acceleration data for the another observation window without determining a step count for the another observation window.

* * * * *